(12) United States Patent
Bhola et al.

(10) Patent No.: US 10,531,885 B2
(45) Date of Patent: Jan. 14, 2020

(54) MEDICAL RETRIEVAL DEVICE

(71) Applicant: Gyrus ACMI, Inc., Southborough, MA (US)

(72) Inventors: Shweta Bhola, Framingham, MA (US); Bruce W. Flight, Melrose, MA (US)

(73) Assignee: Gyrus ACMI Inc., Southborough, MA (US)

( * ) Notice: Subject to any disclaimer, the term of this patent is extended or adjusted under 35 U.S.C. 154(b) by 0 days.

(21) Appl. No.: 16/094,548

(22) PCT Filed: Apr. 19, 2016

(86) PCT No.: PCT/IB2016/052218
§ 371 (c)(1),
(2) Date: Oct. 18, 2018

(87) PCT Pub. No.: WO2017/182840
PCT Pub. Date: Oct. 26, 2017

(65) Prior Publication Data
US 2019/0142441 A1 May 16, 2019

(51) Int. Cl.
*A61B 17/221* (2006.01)
*A61B 17/00* (2006.01)
*A61B 1/00* (2006.01)

(52) U.S. Cl.
CPC ........ *A61B 17/221* (2013.01); *A61B 1/00087* (2013.01); *A61B 2017/00867* (2013.01); *A61B 2017/2212* (2013.01)

(58) Field of Classification Search
CPC . A61B 17/221; A61B 17/26; A61B 17/32056; A61B 17/22031; A61B 17/12022–12195; A61B 2017/2212; A61B 2017/2217; A61B 2017/00358; A61B 2017/00632; A61B 2018/1407; A61B 2018/141; A61F 2002/016
See application file for complete search history.

(56) References Cited

U.S. PATENT DOCUMENTS 3,108,593 A * 10/1963 Glassman ............ A61B 17/221 606/127
4,612,931 A * 9/1986 Dormia ................ A61B 17/221 606/127

(Continued)

FOREIGN PATENT DOCUMENTS

JP 2997484 B2 1/2000

*Primary Examiner* — Elizabeth Houston
*Assistant Examiner* — Charles M Wei
(74) *Attorney, Agent, or Firm* — Harrington & Smith

(57) ABSTRACT

A medical retrieval tool including a sheath; and a basket device connected to the sheath. The basket device includes a shaft and a basket located at a distal end of the shaft. The shaft is movably located in the sheath. The basket includes a first basket cage section and a second basket cage section. The first basket cage section is located in front of the second basket cage section. The basket is configured to be extended from a distal end of the sheath in a plurality of deployment modes including a first deployment mode where the first basket cage section is deployed in a first fully expanded shape and the second basket cage section is located in the sheath; and a second deployment mode where both the first basket cage section and the second basket cage section are deployed out of the distal end of the sheath.

2 Claims, 3 Drawing Sheets

(56) References Cited

U.S. PATENT DOCUMENTS

| | | | | |
|---|---|---|---|---|
| 6,099,534 | A * | 8/2000 | Bates | A61B 17/221 606/113 |
| 6,348,056 | B1 * | 2/2002 | Bates | A61B 17/221 604/22 |
| 6,764,499 | B2 | 7/2004 | Honey et al. | 606/207 |
| 8,211,115 | B2 | 7/2012 | Cheng et al. | 606/114 |
| 8,419,749 | B2 * | 4/2013 | Shelton, IV | A61B 17/00234 606/127 |
| 8,801,748 | B2 * | 8/2014 | Martin | A61B 17/221 606/200 |
| 8,852,205 | B2 * | 10/2014 | Brady | A61B 17/221 606/114 |
| 2001/0051810 | A1 * | 12/2001 | Dubrul | A61B 17/221 606/159 |
| 2014/0214072 | A1 * | 7/2014 | Eidenschink | A61F 2/013 606/200 |
| 2014/0276922 | A1 * | 9/2014 | McLain | A61B 17/221 606/128 |
| 2015/0374483 | A1 * | 12/2015 | Janardhan | A61M 29/00 606/200 |
| 2017/0112513 | A1 * | 4/2017 | Marchand | A61B 17/320725 |
| 2018/0092767 | A1 * | 4/2018 | Pung | A61F 2/966 |

* cited by examiner

MEDICAL RETRIEVAL DEVICE

This patent application is a U.S. National Stage application of International Patent Application Number PCT/IB2016/052218 filed Apr. 19, 2016, which is hereby incorporated by reference in its entirety.

BACKGROUND

Technical Field

The exemplary and non-limiting embodiments relate generally to an endoscope and, more particularly, to an apparatus used with an endoscope.

Brief Description of Prior Developments

U.S. Pat. No. 6,764,499 discloses a medical device with a basket. U.S. Pat. No. 8,211,115 discloses a variable size retrieval basket.

SUMMARY

The following summary is merely intended to be exemplary. The summary is not intended to limit the scope of the claims.

In accordance with one aspect, an example embodiment is provided in a medical retrieval tool comprising a sheath; and a basket device connected to the sheath, where the basket device comprises a shaft and a basket located at a distal end of the shaft, where the shaft is movably located in the sheath. The basket comprises a first basket cage section and a second basket cage section and the first basket cage section is located in front of the second basket cage section. The basket is configured to be extended from a distal end of the sheath in a plurality of deployment modes comprising: a first deployment mode where the first basket cage section is deployed in a first fully expanded shape and the second basket cage section is located in the sheath; and a second deployment mode where both the first basket cage section and the second basket cage section are deployed out of the distal end of the sheath.

In accordance with another aspect, an example method comprises providing a basket device, where the basket device comprises a basket formed by a plurality of legs comprising superelastic material, where the legs are connected at distal ends of the legs; shape setting, by a first heat setting, at least a first portion of the legs to have a first shape; and shape setting, by a second heat setting, at least a second portion of the legs to have a second different shape.

In accordance with another aspect, an example method comprises forming a basket device, where the basket device comprises a basket at a distal end of a shaft, where the basket comprises a plurality of legs forming a first shape with a first basket cage section and a second basket cage section, where the first basket cage section is located in front of the second basket cage section, and where the first basket cage section is smaller than the second basket cage section; and shape setting at least a portion of the basket to have a different second shape when the basket is subjected to a shape-memory transition stress and/or temperature, where the different second shape comprises a basket cage which is larger than the second basket cage section.

BRIEF DESCRIPTION OF THE DRAWINGS

The foregoing aspects and other features are explained in the following description, taken in connection with the accompanying drawings, wherein.

DETAILED DESCRIPTION OF EMBODIMENTS

Figure 1:
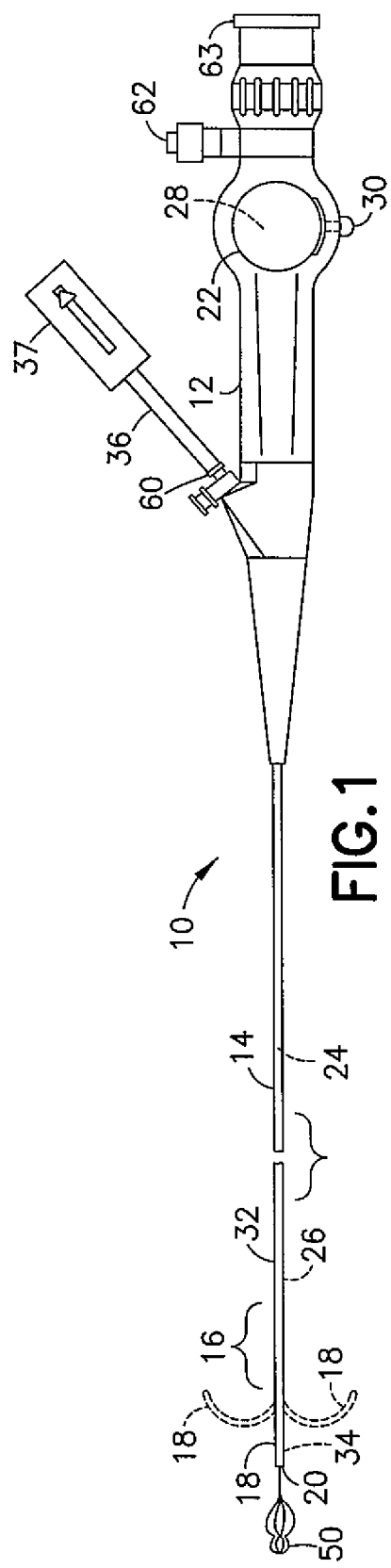
FIG. 1 is a side view of an endoscope.

Referring to FIG. 1, there is shown a side elevation view of an apparatus 10 incorporating features in an example embodiment. Although the present invention will be described with reference to the embodiments shown in the drawings, it should be understood that the present invention can be embodied in many alternate forms of embodiments. In addition, any suitable size, shape or type of elements or materials could be used.

The apparatus 10 in this example is an endoscope medical device configured to be partially inserted into a patient's body, such as in through the patient's urethra for example. The endoscope 10 generally comprises a control section 12 and a flexible or semi-flexible shaft connected to the control section 12. The control section 12 forms a handle for the apparatus. The shaft 14 includes a passive deflection section 16 and an active deflection section (bending section) 18 at the distal end of the shaft 14. A control system 22 to control the active deflection section 18 extends from the control section 12 to the active deflection section 18. The control system 22 generally comprises bending control wires, wire sheaths, and an actuator 28. The wires are connected to the actuator 28 at one end and are connected to the active deflection section 18 at a second end.

In the example embodiment shown, the control section 12 has a user operated slide or lever (control lever) 30. The lever 30 is connected to the actuator 28. The actuator 28 is adapted to pull and release the wires of the control system 22. When the lever 30 is moved by the user, the actuator 28 is moved. The actuator 28 may be, for example, a drum or pulley rotatably connected to the control section 12 to pull one wire while releasing the other. In an alternate embodiment, the actuator may be any suitable type of device, such as a rocker arm adapted to pull and release the wires of the control system 22. In another alternate embodiment, where the control system may have two or more pairs of control wires, the control section will have additional actuators and corresponding controls to drive the additional pairs of bending control wires. In still other alternate embodiments, the control section may have knobs with rack and pinion mechanisms or other suitable user operated controls for the control system.

The shaft 14 is cantilevered from the control section 12. The flexible shaft 14 includes the bending control wires of the control system 22, a fiber optic image bundle, a fiber optic illumination bundle, and a working channel. A port 60 for inserting instruments into the working channel 24 of the shaft is located on the control section 12. The control section 12 also has a light source post 62 for connecting a light source (not shown) to the illumination bundle. In addition, the control section 12 has an eyepiece 63 for a user to view an image transmitted by the image bundle from the front end 20. In alternate embodiments, the flexible shaft may house different systems within. The shaft 14 generally comprises a frame 26, a cover 32 and an objective head 34.

Figure 2:
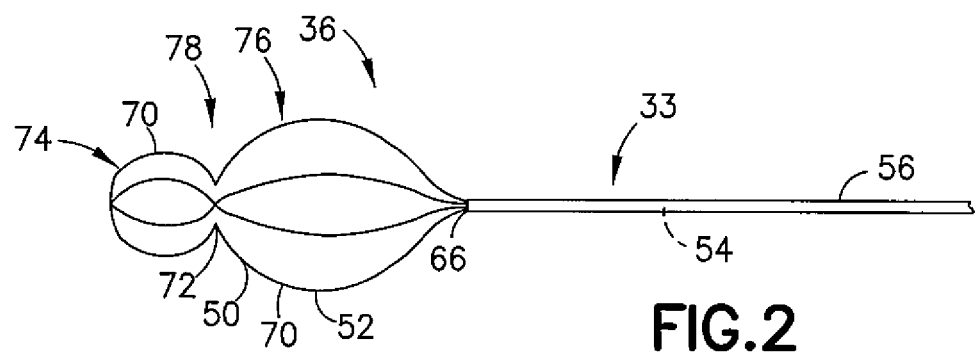
FIG. 2 is a side view of a distal end of an endoscopic tool.
Figure 3:
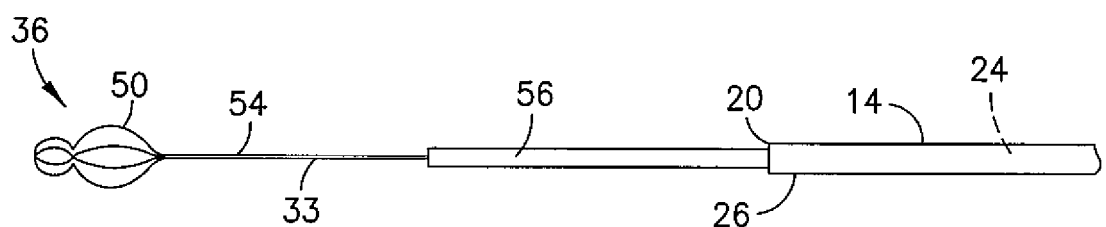
FIG. 3 is a side view illustrating extension of the tool shown in FIG. 2 from the distal end of the endoscope shown in FIG. 1.
Figure 4:
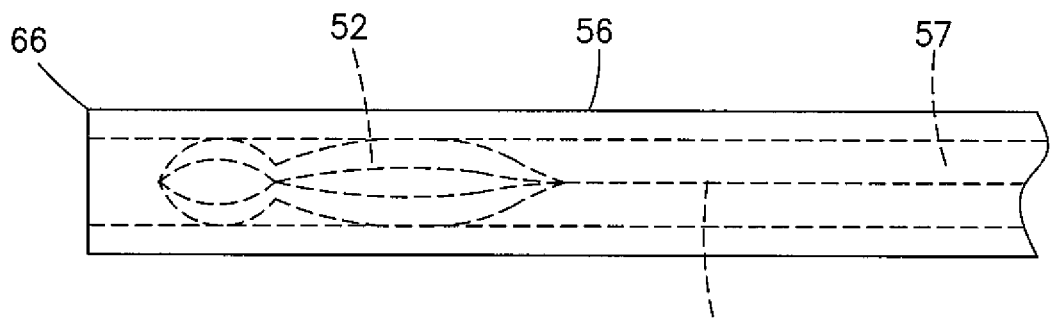
FIG. 4 is a side view of the tool showing the basket device at a retracted position in the sheath of the tool.

Referring also to FIGS. 2-3, a distal end of an endoscopic tool 36 is shown. The tool 36, in this example, is a medical retrieval tool. The tool 36 is attached to the endoscope 10 and is configured to extend out of the distal end 20 of the shaft 14 from the working channel 24. The tool 36 may be a Surgeon Controlled Basket Device (SCBD). The tool 36 includes an assembly 33 which comprises a basket device 50 and a sheath 56. The basket device 50 comprises a basket 52 at a distal end, and a shaft 54 extending through the sheath 56 to a control 37 (see FIG. 1) at a proximal end of the tool 36. The shaft 54 functions as a control wire for moving the basket 52. The control 37 functions as a handle to insert the tool 36 into the working channel 24, and as means to move the basket device 50 and sheath 56 longitudinally relative to each other. The sheath 56 and basket device 50 are longitudinally movable relative to each other to move the basket device 50 between a forward position and a rearward position relative to the sheath 56. FIGS. 2 and 3 show the shaft (control wire) 54 moved forward relative to the sheath 56 such that the basket 52 is located out from a front end aperture 66 of the sheath 56. As shown in FIG. 4, in the forward position of the sheath 56 on the basket device 50, the basket 52 is located inside the channel 57 of the sheath 56; the basket 52 being collapsed by the sheath 56 into a smaller shape to fit inside the sheath 56.

A user, such as a surgeon for example, is able to operate the control 37 to extend the distal end of the tool 36 out of the distal end of the endoscope 10. The user is also able to use the control 37 to move the sheath 56 and basket device 50 relative to each other to deploy the tool, capture an object(s) (such as a kidney stone fragment for example), and retract the object back to the endoscope.

The basket 52 is comprised of a plurality of legs 70. The legs 70 extend from the distal end of the shaft 54 and are connected at a distal end of the basket 52. FIG. 2 shows the legs and basket in their natural home state. The legs 70 have an inwardly bent section 72. This helps to define a first basket cage section 74 and a second basket cage section 76. The inwardly bent sections 72 define a reduced size neck 78 between the two basket cage sections 74, 76. In the example embodiment shown, the legs 70 are comprised of superelastic material or shape memory alloy, such as NITINOL for example. However, other materials might be used. The legs 70 are able to resiliently compress. The legs 70 have internal spring forces to be able to return to their normal size and shape when located out of the sheath.

Figure 5:
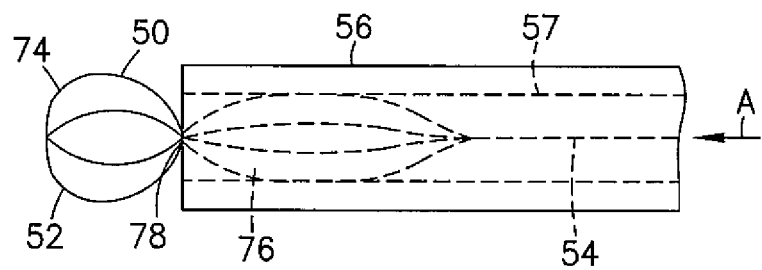
FIG. 5 is a side view of the tool showing the basket device at a first deployed configuration.

As noted above, the basket 52 may be collapsed inside the sheath 56 as shown in FIG. 4. This helps to allow easy insertion of the tool 36 through the working channel 24 of the endoscope 10. Referring also to FIG. 5, the basket device 50 may be moved relative to the sheath 56, as indicated by arrow A, to extend the basket 52 from the distal end of the sheath 56. FIG. 5 shows a first deployed position of the basket 52 relative to the sheath 56. In this first deployed position, only a portion of the basket 52 is extended from the front end of the sheath. In particular, the first basket cage section 74 is deployed as shown. The legs 70 open at the first basket cage section 74 to allow the first basket cage section 74 to open. This allows the first basket cage section 74 to capture an item, such as a stone fragment, therein. In one example, the first basket cage section 74 might be 6 mm in diameter in order to be able to capture a fragment about 1 mm to 3-4 mm in size. The second basket cage section 76 stays inside the sheath 56 in this first deployed configuration.

It is contemplated that control member 37 may be configured with distinct markings and/or locking points to fix the basket at the first, second, or third deployment configuration and move between any intermediate points as desired to facilitate appropriate control over the basket in each deployment configuration.

Figure 6:
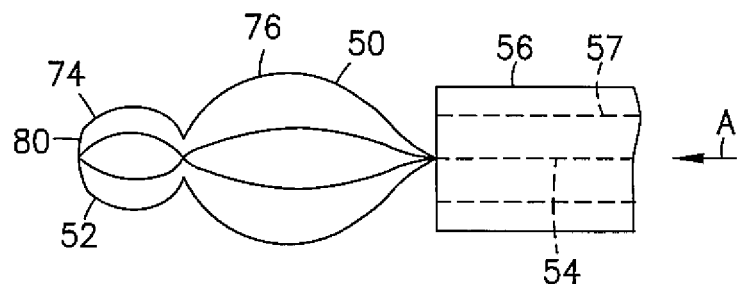
FIG. 6 is a side view of the tool showing the basket device at a second deployed configuration.

Referring also to FIG. 6, the basket device 50 may be further moved relative to the sheath 56, as indicated by arrow A, to extend the basket 52 from the distal end of the sheath 56 a further distance than that shown in FIG. 5. FIG. 6 shows a second deployed position of the basket 52 relative to the sheath 56. In this second deployed position the second basket cage section 76 is fully extended out of the sheath 56 and, thus, is able to spring back into its normal size and shape. This allowed the second basket cage section 76 to be used to capture an item, such as a stone fragment, therein. In one example, the second basket cage section 76 might be mm in diameter in order to be able to capture a fragment larger than that of the first basket cage section. Thus, with features as described in the above example, the basket 52 is sized and shaped to be able to deploy in at least two deployment configurations; with the first basket cage section for capturing smaller items or with the additional second basket cage section for capturing larger items.

Figure 7:
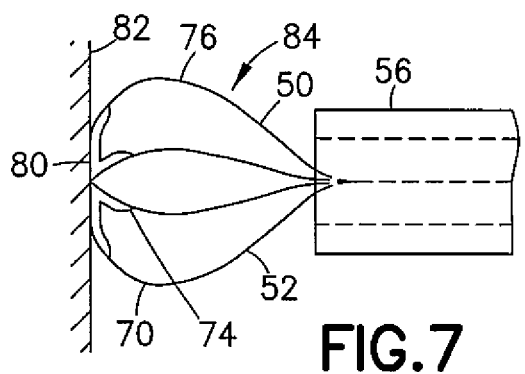
FIG. 7 is a side view of the tool showing the basket device at a third deployed configuration.

Referring also to FIG. 7, the basket 52 may also be configured to deploy into a third deployment configuration. In this example, after deployment into the second deployment configuration shown in FIG. 6, the user may press the distal end 80 of the basket 52 against a surface 82, such as tissue of a patient. The legs 70 are sized, shaped and configured to allow the legs to deform at a predetermined stress to transform into a single basket cage shape rather than the multiple basket cage shapes shown in FIGS. 2 and 6. The construction and geometry of the legs 70, when sufficient force is applied to the end 80, causes the inwardly bent sections 72 to flex outward to change the radius of curvature and push outwards, thereby eliminating the neck 78. This results in a much larger single basket cage section 84 as shown in FIG. 7 with an enlarged diameter, such as about 14 mm for example. The region at the distal tip with a darkened appearance represents the first basket portion 74 in the expanded configuration distally and the second basket portion 76 in the expanded configuration proximally to create the third deployment configuration.

In a conventional basket retrieval device, if the basket captured an item which was too big to withdraw properly with the tool, the user would have to cut the basket away from the endoscope. Features as described herein, on the other hand, provide the ability to enlarge the basket 50 into a third deployment configuration as described above. With this feature, the tool no longer needs to be cut away from the endoscope if the item (stone fragment for example) is too large to be withdrawn through the endoscope. Instead, with features as described herein, the user would capture items with by use of the first and/or second deployments described above, and if the item is too large to be removed through the endoscope working channel 24, the user can implement the third deployment configuration to release the item from the basket 52. The user can then break the item into smaller sizes, such as by lithotripsy for example, and then use the tool 36 to remove the smaller size items through the endoscope's working channel.

The example described above is able to change the shape of the basket 52 by the force applied at the surface 82. However, in an alternate embodiment, other shape memory properties of the superelastic material could be used to trigger the shape change, such as triggering changes between austentite and martensite configurations of NITINOL through stress or temperature changes.

The example described above is able to provide three different capture configurations (FIG. 5, FIG. 6, and FIG. 7). It is contemplated that the configuration of FIG. 7 could also be used as a release configuration. This is able to be accomplished, in the above described example, by providing the basket with two distinct deployable sections 74, 76, as well as use of a shape change capability. With the addition of use of a shape change actuation event (such as the force applied to the end 80 for example), the shape change capability can be used to release a stone which is too large to otherwise be withdraw through the endoscope. In alternate examples, more or less than two different capture configurations could be provided, and more than one release configuration could be provided, and/or more than one shape change actuation event could be provided.

An example embodiment may be provided in a medical retrieval tool comprising a sheath; and a basket device connected to the sheath, where the basket device comprises a shaft and a basket located at a distal end of the shaft, where the shaft is movably located in the sheath. The basket may comprise a first basket cage section 74 and a second basket cage section 76. The first basket cage section may be located in front of the second basket cage section. The basket may be configured to be extended from a distal end of the sheath in a plurality of deployment modes comprising: a first deployment mode where the first basket cage section is deployed in a first fully expanded shape and the second basket cage section is located in the sheath; and a second deployment mode where both the first basket cage section and the second basket cage section are deployed out of the distal end of the sheath.

The basket device may comprise a plurality of legs joined at the shaft and joined at a distal end of the basket device, where the plurality of legs form the first and second basket sections, and where the plurality of legs each have an inwardly bent section forming a reduced size neck between the first and second basket sections. When the basket is in the second deployment mode, and when a front end of the basket is pressed against a surface with a predetermined force, the first and second basket cage sections may be configured to change shape into a single basket cage section which is larger than the second basket cage section. The basket may comprise superelastic material, and the basket may have a distal end which is configured to flatten when the distal end of the basket is pressed against a surface. The first basket cage section may be smaller than the second basket cage section. When in the second deployment mode, the first basket cage section may be about 40-60 percent smaller in size than the second basket cage section. In alternate configurations, the first basket cage section may be larger than the second basket cage section. The plurality of deployment modes may comprise a third deployment mode and, when in the third deployment mode, and the basket may have a single basket shape with a size about 15-35 percent larger than the second basket cage section in the second deployment mode.

It is contemplated that the first basket portion may be configured with lower hoop stress or lower bending stiffness than the second basket portion. It is contemplated that the first basket portion may be configured with a reduced diameter wire, may be chemically etched, may be electro polished, may be flattened, and/or may be provided with a modified cross section such that the bending stiffness may be reduced in the first basket portion. Modifying the basket wire of the first basket portion in this way may eliminate the need for a two-step heat treatment process. In this example configuration, it is contemplated that only a single heat treatment step may accomplish to desired structural change from the second deployment configuration to the third deployment configuration upon the application of pressure at a distal end of the basket section.

It is contemplated that the basket may comprise a first basket portion that is separately heat treated and a second basket portion that is separately heat treated. Subsequently, the first and second basket portions would be joined by welding, or some other method known in the art.

An example method may comprise providing a basket device, where the basket device comprises a basket formed by a plurality of legs comprising superelastic material, where the legs are connected at distal ends of the legs; shape setting, by a first heat setting, at least a first portion of the legs to have a first shape; and shape setting, by a second heat setting, at least a second portion of the legs to have a second different shape.

The second shape may comprise a distal end of the basket having a substantially flat shape. The plurality of legs may comprise superelastic material, and where the basket may have a distal end which is configured to flatten when the distal end of the basket is pressed against a surface. The legs may be shaped into a first basket cage section and a second basket cage section, where the first basket cage section is located in front of the second basket cage section, where the plurality of legs are joined at a shaft of the basket device and joined at a distal end of the basket device, and where the plurality of legs each have an inwardly bent section forming a reduced size neck between the first and second basket sections. The legs may be shape memory trained such that, when a front end of the basket is pressed against a surface with a predetermined force, the first and second basket cage sections are configured to change shape into a single basket cage section which is larger than the second basket cage section. The first basket cage section may be formed smaller than the second basket cage section. The first basket cage section may be about 40-60 percent smaller in size than the second basket cage section and the legs are trained such that, when a distal end of the basket is pressed against a surface with a predetermined force, the basket resiliently deforms into a single basket shape with a size about 15-35 percent larger than the second basket cage section.

An example method may comprise forming a basket device, where the basket device comprises a basket at a distal end of a shaft, where the basket comprises a plurality of legs forming a first shape with a first basket cage section and a second basket cage section, where the first basket cage section is located in front of the second basket cage section, and where the first basket cage section is smaller than the second basket cage section; and shape setting, by heat setting, at least a portion of the basket to have a different second shape when the basket is subjected to a shape-memory transition stress and/or temperature, where the different second shape comprises a basket cage which is larger than the second basket cage section. Features as described herein may be used to provide an adjustable flexible stone retrieval basket, such as with a NITINOL basket for example. Features as described herein may be used to provide a stone retrieval device comprising a basket, a sheath and a handle. The basket may be made of NITINOL wires that are set to assume the shape of the cage. In its normal state the NITINOL wires will always assume the shape of the cage that it was set to, but when the basket is drawn into a plastic sheath then the wires collapse and, thus, the basket closes. An issue with conventional baskets is that they attain the desired shape only at full deployment. With conventional baskets, a cage shape at partial deployment is not ideal for capturing small stones. With features as described herein, the proposed product will have a desirable shape when only partially extended out of the sheath, as well as a different desirable shape when fully extended out of the sheath. This will provide a multi-shape and multi-deployment advantage in order to ease capture of either small stones or large stones.

Features as described herein may be provided with a composite basket cage having a small basket cage located in front of a larger basket cage. When the device is partially deployed, only the small basket cage will come out of the sheath and aid in capture of smaller stones. When the basket is fully deployed the entire composite structure is out of sheath. In addition, when this basket is pressed against the anatomy of a patient, then the small basket can flatten out and combine the two basket cages to become part of an even larger single basket cage.

An example embodiment may be provided in a medical retrieval tool comprising a sheath; and a basket device connected to the sheath, where the basket device comprises a shaft and a basket located at a distal end of the shaft, where the shaft is movably located in the sheath. The basket may comprise means for a first deployment relative to the sheath providing a fully formed first basket cage section, means for a second deployment relative to the sheath providing a fully formed second basket cage section distinct from the first basket cage section, and means for transforming the first and second basket cage sections into a relatively large basket cage formed by a combination of the first and second basket cage sections and resilient deformation of a neck between the first and second basket cage sections.

Features as described herein may be provided with a retrieval device comprising: a first basket portion; a second basket portion; and an outer sheath, wherein the retrieval device is capable of at least a first deployment and a second deployment. The basket may further comprise a third deployment with a flat atraumatic distal end. The first deployment may produce the first basket portion with a smaller basket circumference, and the second deployment may produce the second basket portion with a larger basket circumference.

An example manufacturing method may comprise applying a first heat setting step to a NITINOL basket; and applying a second heat setting step to the NITINOL basket to form the basket with a flat distal end.

It should be understood that the foregoing description is only illustrative. Various alternatives and modifications can be devised by those skilled in the art. For example, features recited in the various dependent claims could be combined with each other in any suitable combination(s). In addition, features from different embodiments described above could be selectively combined into a new embodiment. Accordingly, the description is intended to embrace all such alternatives, modifications and variances which fall within the scope of the appended claims.

What is claimed is:

1. A medical retrieval tool comprising:
a sheath; and
a basket device connected to the sheath, where the basket device comprises a shaft and a basket located at a distal end of the shaft, where the shaft is movably located in the sheath;
where the basket comprises a first basket cage section and a second basket cage section, where the first basket cage section is located in front of the second basket cage section, where the basket is configured to be extended from a distal end of the sheath in a plurality of deployment modes comprising:
a first deployment mode where the first basket cage section is deployed in a first fully expanded shape and the second basket cage section is located in the sheath; and
a second deployment mode where both the first basket cage section and the second basket cage section are deployed out of the distal end of the sheath,
where, when the basket is in the second deployment mode, and when a front end of the basket is pressed against a surface with a predetermined force, the first and second basket cage sections are configured to change shape into a single basket cage section which is larger than the second basket cage section.

2. A method comprising:
providing a basket device, where the basket device comprises a basket formed by a plurality of legs comprising superelastic material;
shape setting, by a first heat setting, at least a first portion of the legs to have a first shape; and
shape setting, by a second heat setting, at least a second portion of the legs to have a second different shape,
where the legs are shaped into a first basket cage section and a second basket cage section, where the first basket cage section is located in front of the second basket cage section, where the plurality of legs are joined at a shaft of the basket device and joined at a distal end of the basket device, and where the plurality of legs each have an inwardly bent section forming a reduced size neck between the first and second basket sections,
where the legs are trained such that, when a front end of the basket is pressed against a surface with a predetermined force, the first and second basket cage sections are configured to change shape into a single basket cage section which is larger than the second basket cage section.

* * * * *